(12) United States Patent
Fowler

(10) Patent No.: US 9,857,310 B2
(45) Date of Patent: *Jan. 2, 2018

(54) METHOD AND SYSTEM FOR TESTING SODIUM DIMETHYLDITHIOCARBAMATE IN WATER

(71) Applicant: Randy Fowler, Cleveland, TN (US)

(72) Inventor: Randy Fowler, Cleveland, TN (US)

(*) Notice: Subject to any disclaimer, the term of this patent is extended or adjusted under 35 U.S.C. 154(b) by 0 days.

This patent is subject to a terminal disclaimer.

(21) Appl. No.: 14/791,711

(22) Filed: Jul. 6, 2015

(65) Prior Publication Data

US 2015/0377790 A1   Dec. 31, 2015

Related U.S. Application Data

(63) Continuation-in-part of application No. 13/744,555, filed on Jan. 18, 2013, now Pat. No. 9,097,680.

(51) Int. Cl.
*G01N 21/79* (2006.01)
*G01N 21/78* (2006.01)
*G01N 33/18* (2006.01)

(52) U.S. Cl.
CPC ............. *G01N 21/78* (2013.01); *G01N 21/79* (2013.01); *G01N 33/182* (2013.01)

(58) Field of Classification Search
CPC ......... G01N 21/79; G01N 21/78; G01N 33/18
USPC .......... 422/408, 430; 436/106, 112, 119–12, 436/163
See application file for complete search history.

(56) References Cited

U.S. PATENT DOCUMENTS

| 3,653,839 | A | | 4/1972 | Luks et al. |
| 3,966,601 | A | * | 6/1976 | Stevenson ............. C02F 1/5236 210/710 |
| 4,021,933 | A | * | 5/1977 | Hughes .................. G09B 23/00 434/262 |
| 4,061,469 | A | * | 12/1977 | DuBose ........... G01N 35/00594 356/39 |
| 4,070,281 | A | | 1/1978 | Tagashira et al. |
| 4,303,610 | A | | 12/1981 | Sardisco et al. |

(Continued)

OTHER PUBLICATIONS

Randhawa, S. S. et al, Journal of Automatic Chemistry 1992, 14, 185-188.*

(Continued)

*Primary Examiner* — Arlen Soderquist
(74) *Attorney, Agent, or Firm* — Chambliss, Bahner & Stophel, P.C.

(57) ABSTRACT

A water testing system having a water sample container that is adapted to retain a water sample, a color indicator container that is adapted to dispense a color indicator which is adapted change the color of the water sample when the water sample contains DTC, and a colorimeter that is adapted to automatically determine a blank value and the concentration of sodium dimethyldithiocarbamate in the water sample. A method for determining the concentration of DTC in a water sample comprising providing a water testing system, placing the water sample in the water sample container, placing the water sample container in the colorimeter, automatically determining a blank value, adding the color indicator to the water sample, placing the water sample container in the colorimeter, and automatically determining the concentration of DTC in the water sample.

17 Claims, 7 Drawing Sheets

(56) References Cited

U.S. PATENT DOCUMENTS

| | | | |
|---|---|---|---|
| 4,333,908 A | 6/1982 | Maki et al. | |
| 4,882,285 A | 11/1989 | Ogleby et al. | |
| 5,083,868 A * | 1/1992 | Anderson | G01N 21/251 356/402 |
| 5,092,677 A * | 3/1992 | Curtis | G01N 21/255 250/565 |
| 5,298,978 A * | 3/1994 | Curtis | B01L 3/021 250/577 |
| 5,421,967 A | 6/1995 | Tubergen | |
| 5,470,484 A | 11/1995 | McNeel | |
| 5,670,381 A * | 9/1997 | Jou | G01N 33/538 435/7.92 |
| 5,686,237 A * | 11/1997 | Al-Bayati | C12Q 1/37 435/108 |
| 5,726,062 A * | 3/1998 | Numa | G01N 33/52 422/410 |
| 5,856,272 A | 1/1999 | Wilkins, Jr. | |
| 6,613,577 B1 * | 9/2003 | Da Cruz | G01N 31/005 436/12 |
| 7,046,347 B1 * | 5/2006 | Amend | G01N 21/51 356/338 |
| 7,491,546 B2 * | 2/2009 | Jaunakais | G01N 31/224 356/436 |
| 9,097,680 B1 * | 8/2015 | Fowler | G01N 33/18 |
| 2003/0201224 A1 | 10/2003 | Gannon et al. | |
| 2004/0137553 A1 * | 7/2004 | Coates | C12Q 1/28 435/28 |
| 2006/0073603 A1 * | 4/2006 | Jaunakais | G01N 31/224 436/125 |
| 2006/0286242 A1 * | 12/2006 | Villagran | A21D 2/366 426/549 |
| 2008/0190354 A1 * | 8/2008 | Malpas | G01N 21/293 116/206 |
| 2010/0150842 A1 * | 6/2010 | Ravn | G01N 33/5097 424/9.2 |
| 2011/0063433 A1 * | 3/2011 | Thonhauser | G01N 21/251 348/135 |
| 2012/0014902 A1 * | 1/2012 | Carty | A01N 59/00 424/76.2 |

OTHER PUBLICATIONS

Yang, H. et al, Measurement 2008, 41, 44-54.*
Callan, T. et al, Analyst 1929, 54, 650-653.*
McFarlane, W. D., Biochemical Journal 1932, 26,1022-1033.*
Domar, G. et al, Acta Chemica Scandinavica 1949, 3, 1441-1442.*
Wyatt, P. F., Analyst 1953,78, 656-661.*
Chilton, J. M. et al, Analytical Chemistry 1953, 25, 1274-1275.*
Iijima, T. et al, Nippon Gomu Kyokaishi 1956, 29, 551-555.*
Akerstrom, S. et al, Acta Chemica Scandinavica 1962, 16, 1206-1211.*
Onuska, F. T., Analytical Letters 1974, 7, 327-334.*
Wing, R. E. et al, Plating and Surface Finishing 1982, 69, 67-71.*
Malik, A. K. et al, Talanta 1990, 37, 1205-1207.*
Malik, A. K. et al, Pesticide Science 1999, 55, 965-970.*
Gartiser, S. et al, Environmental Science and Pollution Research 2010, 17, 1149-1157.*
Irth, H. et al, Journal of Chromatography 1986, 370, 439-447.*
Malik, A. K. et al, Indian Journal of CHemistry 1991, 30A, 986-988.*
Malik, A. K. et al, Journal of Surface Science and Technology 1996, 12, 23-28.*
Taguchi, S. et al, Analytical Science 1999, 15, 1149-1152.*
Sharma, V. K. et al, International Journal of Environmental Analytical Chemistry 2004, 84, 1105-1110.*
Hach Pocket ColorimeterTM II Data Sheet 2009, 4 pages.*
Hach DR/800 Series Colorimeters Data Sheet 2009, 8 pages.*
Stevenson, A. Journal of the Science of Food and Agriculture 1964, 15, 509-522.
Nitowski, A. J. et al, Journal of Chromatography A 1997, 781, 541-545.
Malik, A. K. et al, Pesticide Science 1998, 53, 104-106.
Cao, X. et al, Analytical Methods 2012, 4, 2996-3001.
Moss, J. "Variable Technologies wins Early Innovator Award" Buisness Chatt Nov. 13, 2012, 5 pages dowloaded from http://businesschatt.com/2012/11/variable-technologies . . . .

* cited by examiner

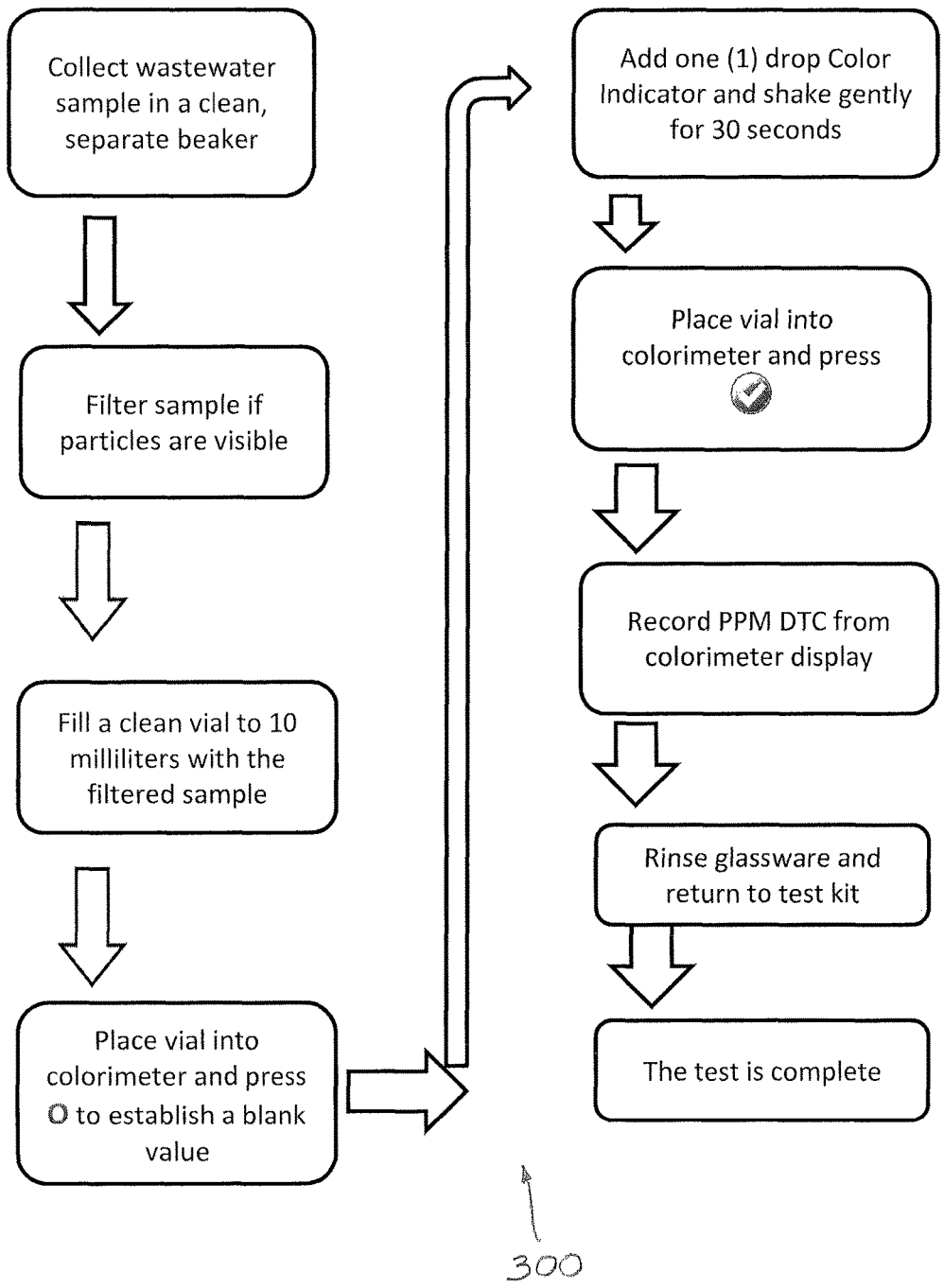

METHOD AND SYSTEM FOR TESTING SODIUM DIMETHYLDITHIOCARBAMATE IN WATER

CROSS-REFERENCES TO RELATED APPLICATIONS/PATENTS

This application is a continuation-in-part application that relates back to and claims the benefit of priority from U.S. patent application Ser. No. 13/744,555 entitled "Apparatus and Method for Determining Sodium Dimethyldithiocarbamate in Water" and filed on Jan. 18, 2013, now U.S. Pat. No. 9,097,680.

FIELD OF THE INVENTION

The present invention relates generally to water testing systems, and particularly to water testing systems adapted to determine the concentration of sodium dimethyldithiocarbamate (DTC) in industrial water.

BACKGROUND AND DESCRIPTION OF THE PRIOR ART

It is known to test water to determine the concentration of sodium dimethyldithiocarbamate in the water. Conventional tests, however, suffer from one or more disadvantages. For example, conventional tests require large, heavy, expensive equipment that must be calibrated on a daily basis and materials that are expensive and difficult to purchase. Conventional tests are also complex and require extensive formal training before they can be performed. Further, conventional tests require undesirable delays in receiving the results of the tests. Still further, conventional tests are not sufficiently automated and are subject to human error.

It would be desirable, therefore, if an apparatus and method for a water testing system could be provided that is compact, light-weight, portable and inexpensive. It would also be desirable if such a water testing system could be provided that uses inexpensive, easily accessible materials and does not require daily calibration. It would be further desirable if such a water testing system could be provided that is simple and does not require extensive formal training. It would be still further desirable if such a water testing system could be provided that produces timely results. In addition, it would be desirable if such a water testing system was automated and not subject to human error.

Advantages of the Preferred Embodiments of the Invention

Accordingly, it is an advantage of the preferred embodiments of the invention claimed herein to provide an apparatus and method for a water testing system that is compact, light-weight, portable and inexpensive. It is also an advantage of the preferred embodiments of the invention claimed herein to provide and apparatus and method for a water testing system that uses inexpensive, easily accessible materials and does not require daily calibration. It is another advantage of the preferred embodiments of the invention claimed herein to provide an apparatus and method for a water testing system that is simple and does not require extensive training. It is a further advantage of the preferred embodiment of the invention claimed herein to provide an apparatus and method for a water testing system that produces timely results. It is a still further advantage of the preferred embodiments of the invention described and claimed herein to provide an apparatus and method for a water testing system that is automated and not susceptible to human error.

Additional advantages of the preferred embodiments of the invention will become apparent from an examination of the drawings and the ensuing description.

Explanation of the Technical Terms

As used herein, the term "water" includes any type of fluid in which sodium dimethyldithiocarbamate may be contained, including without limitation, industrial and municipal wastewater, agricultural irrigation water, ground water, natural bodies of water and the like.

SUMMARY OF THE INVENTION

The apparatus of the invention comprises a water testing system for determining the concentration of sodium dimethyldithiocarbamate in a water sample. The preferred water testing system comprises a water sample container adapted to receive the water sample, a color indicator container adapted to dispense a color indicator which is adapted change the color of the water sample when the water sample includes sodium dimethyldithiocarbamate, and a colorimeter adapted to receive the water sample container and determine a blank value and a sodium dimethyldithiocarbamate concentration for the water sample. In the preferred embodiments of the water testing system, the colorimeter automatically determines the blank value and the sodium dimethyldithiocarbamate concentration for the water sample.

The method of the invention comprises a method for determining the concentration of sodium dimethyldithiocarbamate in a water sample. The preferred method comprises providing a water testing system. The preferred water testing system comprises a water sample container adapted to retain the water sample, a color indicator container adapted to dispense a color indicator, and a colorimeter adapted to receive the water sample container. The preferred method further comprises placing the water sample in the water sample container, placing the water sample container in the colorimeter, automatically determining a blank value, adding the color indicator to the water sample, placing the water sample container in the colorimeter, and automatically determining the concentration of sodium dimethyldithiocarbamate in the water sample.

BRIEF DESCRIPTION OF THE DRAWINGS

The presently preferred embodiments of the invention are illustrated in the accompanying drawings, in which like reference numerals represent like parts throughout, and in which:

FIG. 11 is a flow chart illustrating a first alternative method for determining the concentration of DTC in a water sample in accordance with the present invention.

DESCRIPTION OF THE PREFERRED EMBODIMENTS OF THE INVENTION

Figure 3:
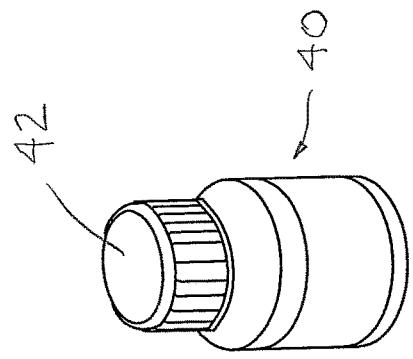
FIG. 3 is a perspective view of the preferred titration reagent container in accordance with the present invention.

Referring now to the drawings, the preferred embodiments of the apparatus and method for a water testing system in accordance with the present invention are illustrated by FIGS. 1 through 11. As shown in FIGS. 1-11, the preferred embodiments of the apparatus and method for a water testing system are adapted to be compact, light-weight, portable and inexpensive quantitative field analytical water testing system. The preferred embodiments of the apparatus and method for a water testing system are also adapted to use inexpensive, easily accessible materials and do not require daily calibration. The preferred embodiments of the apparatus and method for a water testing system are further adapted to be simple and do not require extensive training. The preferred embodiments of the apparatus and method for a water testing system are still further adapted to produce timely results. In addition, the preferred embodiments of the apparatus and method for a water testing system are adapted to be automated and not susceptible to human error.

Figure 1:
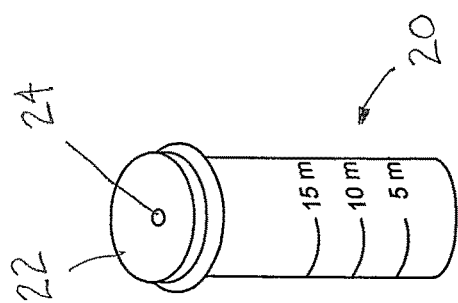
FIG. 1 is a perspective view of the preferred embodiment of the water sample container in accordance with the present invention.

Referring now to FIG. 1, a perspective view of the preferred embodiment of the water sample container of the water testing system in accordance with the present invention is illustrated. As shown in FIG. 1, the preferred water sample container is designated generally by reference numeral 20. The preferred water sample container 20 is adapted to receive, retain and dispense an approximately 15 milliliter (mL) water sample and includes markings such as graduating lines reflecting 5 mL, 10 mL and 15 mL. The preferred water sample container 20 also includes cap 22. Preferred cap 22 is adapted to be removably affixed to the open end of water sample container 20. Preferred cap 22 also includes aperture 24 which is adapted to permit fluid to be added to the water sample retained by water sample container 20. While FIG. 1 illustrates the preferred configuration and arrangement of the water sample container and cap, it is contemplated within the scope of the invention that the water sample container and cap may be of any suitable configuration and arrangement.

Figure 2:
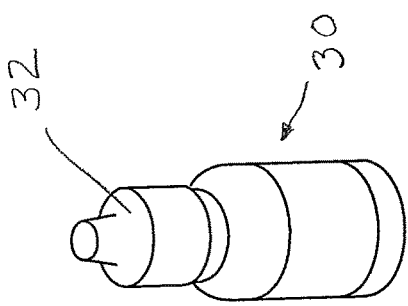
FIG. 2 is a perspective view of the preferred color additive container in accordance with the present invention.

Referring now to FIG. 2, a perspective view of the preferred color additive container of the water testing system in accordance with the present invention is illustrated. As shown in FIG. 2, the preferred color additive container is a drop bottle and designated generally by reference numeral 30. The preferred drop bottle 30 includes bottle cap 32. The preferred drop bottle 30 is adapted to receive, retain and dispense a color indicator. Preferably, drop bottle 30 is adapted to dispense a drop (approximately 0.04545 milliliters) of liquid color indicator at a time. Preferably, a drop of color indicator is added to the 15 mL water sample using drop bottle 30. While FIG. 2 illustrates the preferred configuration and arrangement of the color additive container, it is contemplated within the scope of the invention that the color additive container may be of any suitable arrangement and configuration.

Still referring to FIG. 2, the preferred color indicator is adapted to change the color of a water sample when the water sample includes sodium dimethyldithiocarbamate (DTC). More particularly, the preferred color indicator is adapted to change the color of the water sample from clear to a color ranging from yellow to brown depending upon the concentration of sodium dimethyldithiocarbamate in the water sample. Preferably, the color indicator comprises a 25 w/v % solution of copper sulfate pentahydrate ($CuSO_4.5H_2O$). The molecular weight of the preferred color indicator compound is approximately 249.686 grams. Consequently, a 1 molar (1M or 25%) solution may be prepared by dissolving 250 grams of copper sulfate pentahydrate in approximately 700 mL of deionized water (DI) in a volumetric flask. The flask is then preferably filled to the one liter mark (1,000 mL) with DI and blended thoroughly for a period of approximately 60 minutes or until completely dissolved. It is contemplated within the scope of the invention that the color additive may be of any suitable composition adapted to change the color of a water sample when the water sample contains DTC.

Referring now to FIG. 3, a perspective view of the preferred titration reagent container of the water testing system in accordance with the present invention is illustrated. As shown in FIG. 3, the preferred titration reagent container is adapted receive, retain and dispense a titration reagent and is designated by reference numeral 40. The preferred titration reagent container 40 includes removable reagent cap 42. The preferred titration reagent is adapted to return the water sample and color indicator mixture to an uncolored or clear condition. More particularly, the preferred titration reagent is slowly added, drop-by-drop, to the water sample and color indicator mixture until the water sample is clear. While FIG. 3 illustrates the preferred configuration and arrangement of the titration reagent container, it is contemplated within the scope of the invention that the titration reagent container may be of any suitable configuration and arrangement and that the water testing system comprises more than one titration reagent container.

Still referring to FIG. 3, the preferred titration reagent comprises an approximately 0.2 w/v % (2 grams per liter) solution of sodium hypochlorite (NaOCl). The molecular weight of this compound is approximately 74.4 grams, or 7.44 w/v % in solution. Sodium hypochlorite is available commercially as 6 w/v % (60 g/L, which is 0.806 Molar), 5.25 w/v % (52.5 g/L, which is 0.706 Molar) and industrially as 15 w/v % (150 g/L, which is 2.02 Molar). Sodium hypochlorite is known as generic bleach, laundry bleach, or Clorox® bleach. Preparing a 2 gram per liter (0.27 Molar) solution may be accomplished by pipetting 33.33 milliliters of 6% bleach into a 1000 mL volumetric flask, then filling to the 1000 mL mark with DI and slowly blending on a magnetic stirring table for a period of 60 minutes. While the foregoing describes the preferred composition and method for producing the titration reagent, it is contemplated within the scope of the invention that the titration reagent may be of any suitable composition for determining the concentration of DTC in a water sample and may be produced by any suitable process.

Preferably, the formulating equation for the titration reagent is as follows: 2 g/L NaOCl/60 g/L NaOCl×1,000 mL total volume=33.33 mL NaOCl. Because the desired concentration of sodium hypochlorite solution is 2 g/L (grams per liter), and sodium hypochlorite is available in a concentration of 60 g/L, it is necessary to divide 2 g/L by 60 g/L. The resulting quotient, 0.03333, is then multiplied by 1,000, which is the total volume (1 liter) that DTC reagent is prepared as. It may be prepared in other volumes, but this is the standard volume. The product, 33.33, represents the number of milliliters of 60 g/L sodium hypochlorite solution that is used to make 1 liter by dilution with DI.

Figure 4:
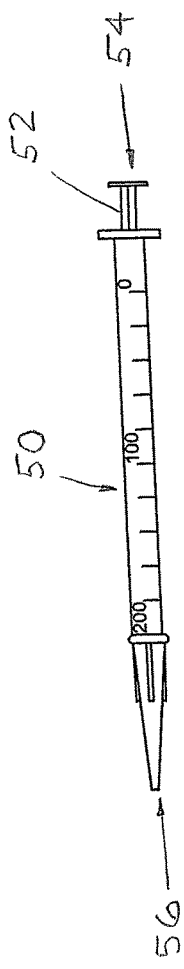
FIG. 4 is a front view of the preferred syringe in accordance with the present invention.

Referring now to FIG. 4, a front view of the preferred titration reagent dispenser of the water testing system in accordance with the present invention is illustrated. The preferred titration reagent dispenser is a syringe and generally designated by reference numeral 50. Preferred syringe 50 includes plunger 52, plunger end 54 and distal end 56. Preferred syringe 50 also comprises graduated numerals ranging from zero (0) to two hundred (200) parts per million and is adapted to hold approximately 1.0 milliliters of titration reagent. Preferred syringe 50 is also adapted to receive, retain and dispense a titration reagent. More particularly, preferred syringe 50 is adapted to add a titration reagent, drop by drop, to a water sample and color indicator mixture. While FIG. 4 illustrates the preferred configuration and arrangement of the titration reagent dispenser, it is contemplated within the scope of the invention that the titration reagent dispenser may be of any suitable arrangement and configuration.

Figure 5:
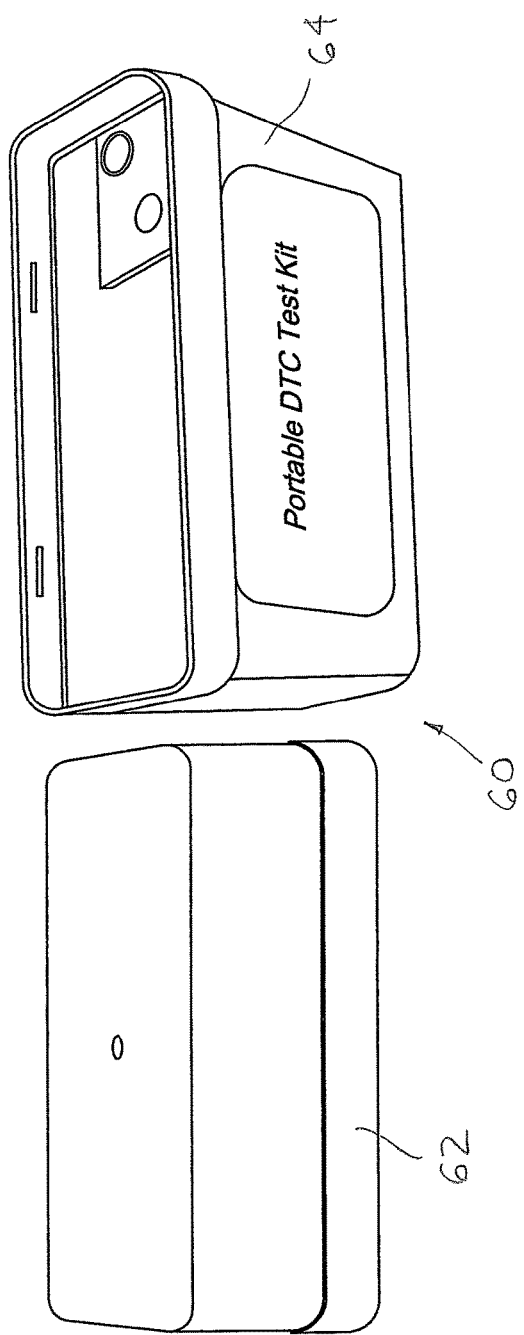
FIG. 5 is a perspective view of the preferred water testing system carrier in accordance with the present invention.

Referring now to FIG. 5, a perspective view of the preferred carrier of the water testing system in accordance with the present invention is illustrated. As shown in FIG. 5, the preferred carrier is designated generally by reference numeral 60. The preferred carrier 60 is adapted to receive water sample container 20, drop bottle 30, titration reagent container 40 and syringe 50. Preferred carrier 60 is adapted to provide a portable water testing system. The preferred carrier 60 includes top portion 62 and bottom portion 64. While FIG. 5 illustrates the preferred configuration and arrangement of the carrier, it is contemplated within the scope of the invention that the carrier may be of any suitable arrangement and configuration.

Figure 6:
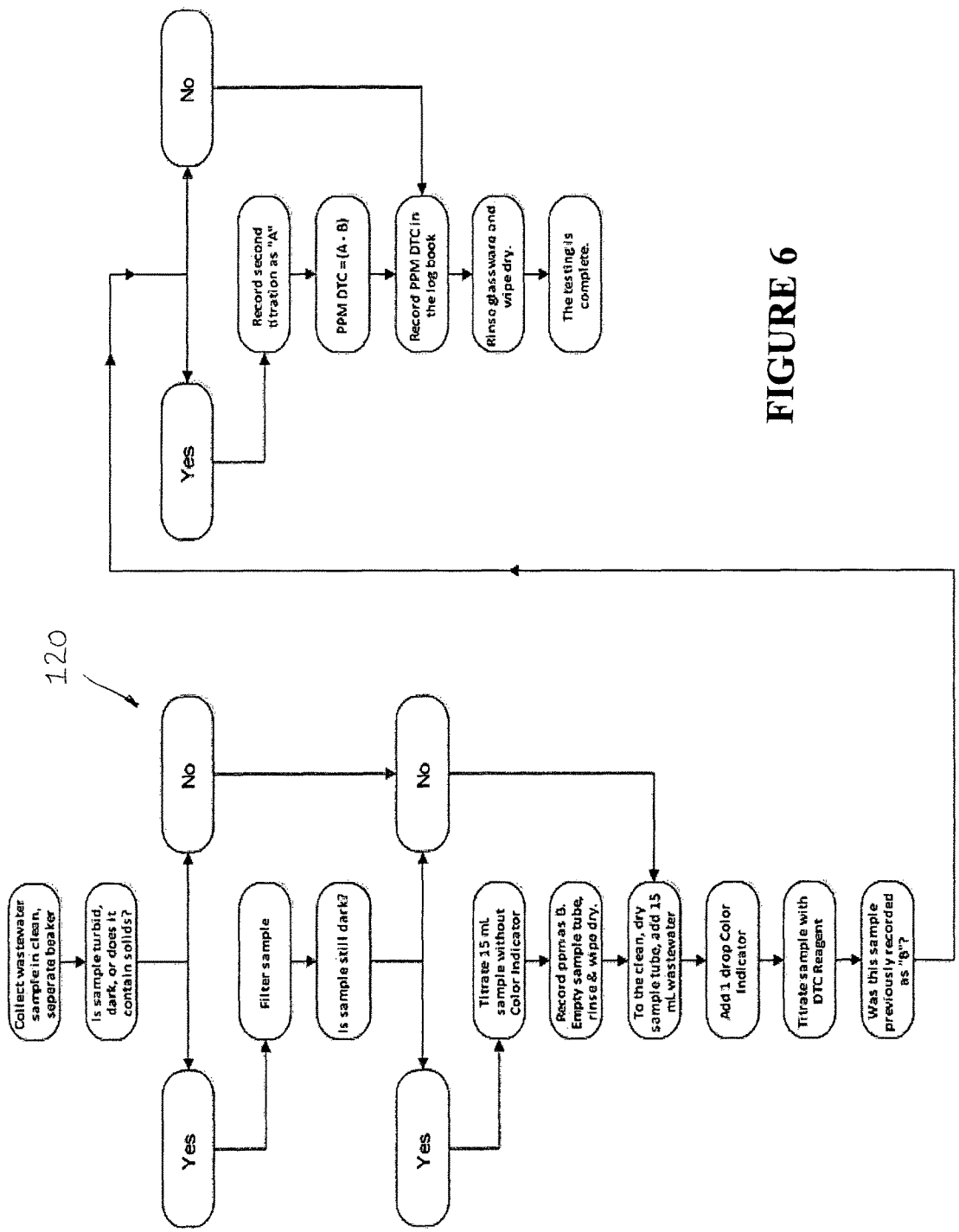
FIG. 6 is a flow chart illustrating the preferred method for determining the concentration of DTC in a water sample in accordance with the present invention.

Referring now to FIG. 6, the invention also comprises a method for determining the concentration of sodium dimethyldithiocarbamate in a water sample. As shown in FIG. 6, the preferred method for determining the concentration of sodium dimethyldithiocarbamate in a water sample is designated generally by reference numeral 120. The preferred method comprises providing a water testing system as described above.

Still referring to FIG. 6, the preferred method also comprises placing a water sample in a water sample container, adding a color indicator to the water sample, adding a titration reagent to the water sample, and determining the concentration of sodium dimethyldithiocarbamate in the water. In the preferred method, a drop or approximately 0.04545 mL of the color indicator is added to a 15 mL water sample. If the water sample contains sodium dimethyldithiocarbamate, the color indicator solution will change the color of the sample from clear to a color ranging from yellow to brown depending upon the concentration of sodium dimethyldithiocarbamate. If the water sample does not change color after the color indicator solution is added, then the sample does not contain any sodium dimethyldithiocarbamate.

Still referring to FIG. 6, in the preferred method, approximately 1.0 mL of titration reagent is added to the syringe, and the titration reagent is added, drop-by-drop, to the water sample and color indicator mixture until the water sample is clear. The syringe is marked such that the distal end of the plunger coincides with the marking representing zero (0) when the syringe contains 1.0 milliliters of titration reagent. The syringe is marked from zero (0) to two hundred (200) parts per million. By slowly applying a force to the plunger while gently swirling the water sample container, the titration reagent is added one drop at a time to the water sample through the aperture in the cap of the water sample container until the water sample returns to its original color, i.e. clear. When the water sample has returned to clear, the distal end of the plunger coincides with marking representing the concentration of sodium dimethyldithiocarbamate contained in the water sample in parts per million.

Still referring to FIG. 6, if the distal end of the plunger coincides with the marking representing 200 ppm before the water sample returns to clear, then the syringe may be refilled with the titration reagent to the zero (0) marking. A force is then slowly applied to the plunger and the titration reagent is added to the water sample until the water sample is clear. When the water sample is clear, the distal end of the plunger coincides with the marking representing the concentration of sodium dimethyldithiocarbamate plus 200 ppm. If the water sample is not clear after 2.0 milliliters of titration reagent are added to the water sample, then the syringe is refilled and 400 ppm is added to the result achieved in the third round. If the water sample is again not clear after emptying the contents of the syringe, the process can be repeated until the water sample returns to a clear condition.

Still referring to FIG. 6, the preferred method also comprises the step of collecting a water sample of approximately 100 mL in a clean beaker or other suitable container means and determining if the water sample is turbid (cloudy) or dark or if it contains solids such as particulates. If any of these conditions exist, the water sample is preferably filtered into another clean container using a coffee filter and a small funnel. It is contemplated within the scope of the invention, however, that any suitable filtering means could be used to filter a water sample that is dark or cloudy or contain particulates. If none of these conditions exist after the water sample is filtered, then the process described above is followed.

If, however, any of these conditions still exist in the water sample after it has been filtered, titration reagent is added to a 15 mL filtered water sample until none of the conditions exist, i.e. the water sample is clear. The amount of titration reagent added to the 15 mL water sample is recorded in terms of ppm (as measured on the syringe) as value "B." The 15 mL water sample is then removed from the water sample container and a second 15 mL water sample from the same filtered water used in the first measurement is placed into the water sample container, a drop of color indicator is added to the water sample, and titration reagent is added drop by drop until the water sample is clear again. Preferably, the water sample container may be gently swirled as the titration reagent is slowly added to the 15 mL water samples. The amount of titration reagent added to the second filtered water sample is again recorded in terms of ppm (as measured on the syringe) as value "A." Then, value B is subtracted from value A to determine the level of DTC in the water sample in terms of ppm. The DTC level can be recorded in a log book or other suitable medium including without limitation an electronic device. After cleaning the water sample container and any other beakers or the like used to collect the water sample, the process may be repeated.

If the water sample collected has a DTC concentration in excess of 2,000 ppm, dark brown precipitates may begin to form. According to an alternative embodiment of the method of the invention, a 5 mL water sample is added to 10 mL of distilled or deionized water and mixed. A drop of color indicator may be added to the water sample and titration reagent may thereafter be added, drop-by-drop, until the water sample is clear. The amount of titration reagent added to the water sample and color indicator mixture is determined in ppm as indicated by the syringe and that amount is multiplied by three (3) to obtain the concentration of DTC in the water sample. While FIG. 6 illustrates the preferred sequence of the steps of the method for determining the concentration of sodium dimethyldithiocarbamate in a water sample, it is contemplated within the scope of the invention that the steps of the method of the invention may be performed in any suitable sequence.

If DTC is being added to an industrial wastewater treatment system by an electronic metering pump, the current pump control settings (PCS) when an effluent water sample is pulled may be recorded. When the sample has been analyzed and the DTC concentration (PPM DTC) has been determined, the desired pump control settings may be calculated using the following equation: Desired PCS=Desired PPM DTC/Existing PPM DTC×Current PCS. By way of example, if the pump speed is set at 100 beats per minute (BPM) and the DTC concentration is determined to be 70 ppm, and a DTC concentration of 10 ppm is desired, the calculation is equated as follows: 10 ppm DTC/70 ppm DTC×100 BPM=14.3 BPM. Thus, in this example, the pump speed should be dropped to about 14 beats per minute. It may still be necessary to repeat the analysis several times to establish the correct pump speed for each individual case.

In most cases, operators who run DTC find that a safe residual DTC concentration is approximately 10 ppm. Typically, DTC is prepared and sold as a liquid solution in which the molecular concentration of sodium dimethyldithiocarbamate is 40%. To determine the actual concentration of the DTC molecule within a tested water sample, one may use the following equation: PPM Actual DTC Molecule in the Water Sample=PPM DTC×0.4. After determining the actual DTC molecule concentration, the Milligrams per Liter (mg/L) of DTC can be calculated using the following equation: Mg/L DTC Molecule=PPM Actual DTC Molecule in the Water Sample×0.8547. Parts per Million (PPM) and Milligrams per Liter (mg/L) are slightly different because DTC has a density of 1.17 g/mL. Consequently, one may calculate mg/L by multiplying PPM by 0.8547.

Figure 7:
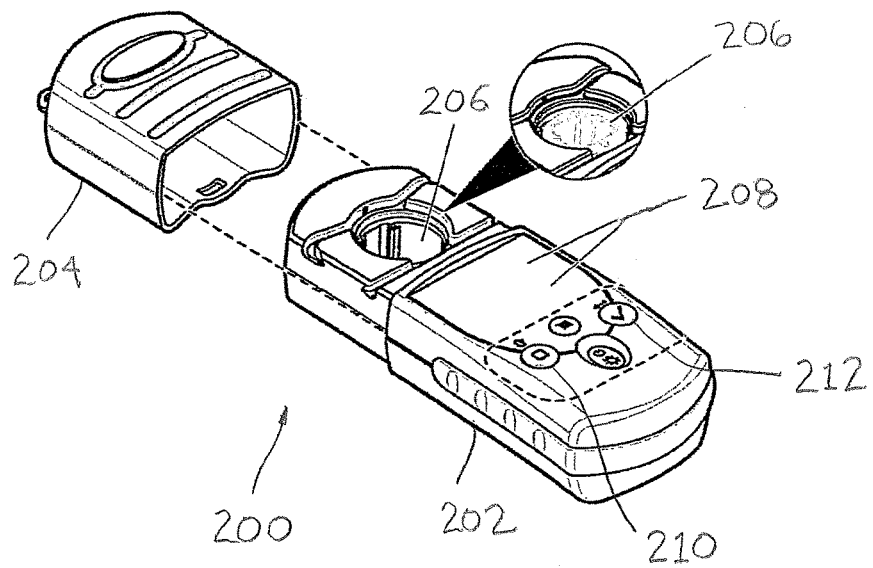
FIG. 7 is a perspective view of an exemplary colorimeter adapted for use in connection with the present invention shown with the colorimeter cap removed.

Referring now to FIG. 7, a perspective view of an exemplary colorimeter adapted for use in connection with the present invention is illustrated. As shown in FIG. 7, the exemplary colorimeter is designated generally by reference numeral 200. Exemplary colorimeter 200 is adapted to measure the absorbance of particular wavelengths of light by a specific solution. Preferably, exemplary colorimeter 200 comprises a light source, an adjustable aperture, a set of colored filters used to select the wavelength of light which a solute absorbs the most, a cuvette to hold a water sample, a detector such as a photoresistor adapted to measure the transmitted light to determine the "darkness" of a water sample, a circuit board adapted to translate the measured "darkness" into a corresponding DTC concentration present in the water sample, and a meter to display the output from the detector. Preferably, exemplary colorimeter 200 is adapted to be programmed such that it will automatically determine the concentration of DTC in a water sample based on the lightness and darkness of the water sample. More particularly, exemplary colorimeter 200 is preferably a digital, programmable, hand-held colorimeter such as a Hach Pocket Colorimeter II.

Still referring to FIG. 7, in order for exemplary colorimeter 200 to automatically determine the DTC concentration in a water sample based on the "darkness" of the sample, the colorimeter must first be programmed. More particularly, exemplary colorimeter 200 has to be set at the wavelength that absorbs the highest amount of the DTC with copper sulfate color. In order to determine the optimal wavelength for the colorimeter, a spectrophotometer may be used. It has been found that the optimal wavelength for absorbing the DTC-copper sulfate color is approximately 472 nanometers, but a wavelength of approximately 450 nanometers has also been found to achieve accurate results. In order to program the colorimeter, a blank sample and a standard sample may be used. More particularly, the blank sample may comprise 10 mL of deionized water and a drop of copper sulfate solution, and the standard sample may comprise 10 mL of a solution containing 200 PPM of DTC. Preferably, the blank sample is placed into the colorimeter and a series of steps are performed before the blank sample is removed from the colorimeter and the standard sample is placed into the colorimeter. After the standard sample is placed into the colorimeter a series of steps are performed before the standard sample is removed from the colorimeter. The blank sample is then preferably placed into the colorimeter again and another step is performed before the blank sample is removed from the colorimeter. Then, the standard sample is preferably placed into the colorimeter again and another step is performed to program the colorimeter to automatically determine the DTC concentration in a water sample. While this paragraph describes the preferred procedures for determining the optimal wavelength for measuring the DTC-copper sulfate color and for programming a colorimeter to automatically determine the DTC concentration in a water sample, it is contemplated within the scope of the invention that any suitable procedures may be used.

Still referring to FIG. 7, exemplary colorimeter 200 comprises base 202 and cap 204. Preferably, cap 204 is removably attached to base 202. Preferred base 202 comprises opening 206, display 208, first button 210, and second button 212. Preferred opening 206 is adapted to receive a water sample container such as container 20 illustrated in FIG. 1. Preferred display 208 is adapted to provide the user with an interface that displays the results of the calculations performed by the programmed colorimeter, including the concentration level of DTC in a tested water sample. Preferred first button 210 is adapted to provide the user with a "blank value," and preferred second button 212 is adapted to provide the user with the concentration level, in parts per million (PPM), of DTC in a tested water sample. More particularly, the "blank value" instructs the colorimeter that the amount of DTC in the sample that has not reacted to the color indicator is equal to zero (0.00). While FIG. 7 illustrates the preferred configuration and arrangement of the colorimeter, it is contemplated within the scope of the invention that the colorimeter may be of any suitable configuration and arrangement.

Figure 8:
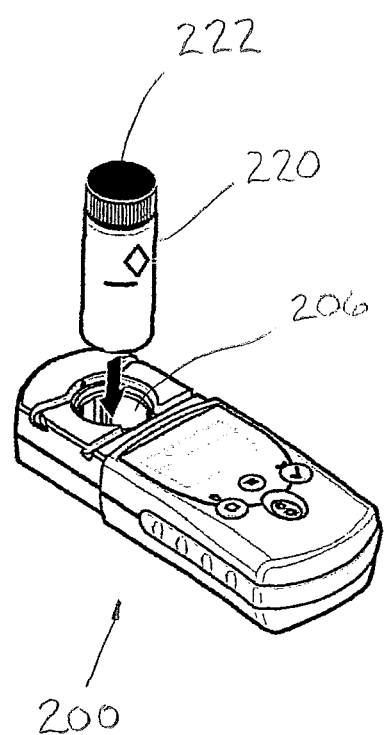
FIG. 8 is a perspective view of the exemplary colorimeter illustrated in FIG. 7 shown with a water sample container.

Referring now to FIG. 8, a perspective view of exemplary colorimeter 200 is illustrated with preferred water sample container 220 having container cap 222. As shown in FIG. 8, preferred water sample container 220 is adapted to be received by opening 206. Preferably, water sample container 220 is adapted to hold a 10 mL water sample. It is contemplated within the scope of the invention, however, that the water sample container may hold a water sample that is larger or smaller than 10 mL.

Figure 9:
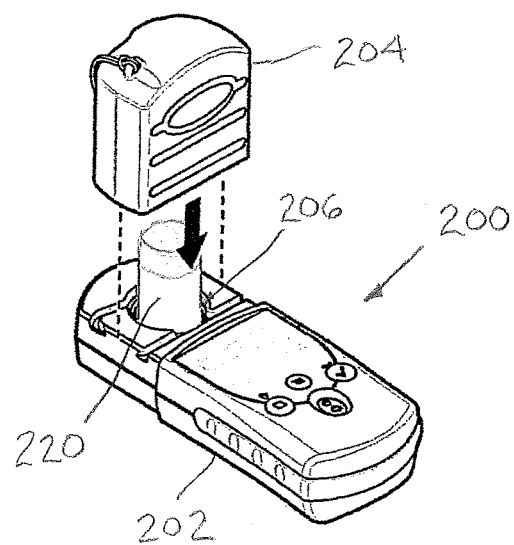
FIG. 9 is a perspective view of the exemplary colorimeter illustrated in FIGS. 7-8 shown with the water sample container inserted into the colorimeter.

Referring now to FIG. 9, a perspective view of exemplary colorimeter 200 is shown with water sample container 220 inserted into opening 206 of the colorimeter. As shown in FIG. 9, colorimeter cap 204 is adapted to be removably attached to base 202 so as to substantially surround water sample container 220.

Figure 10:
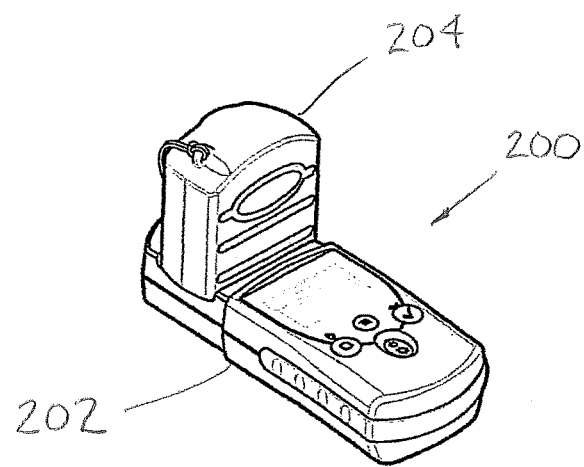
FIG. 10 is a perspective view of the exemplary colorimeter illustrated in FIGS. 7-9 shown with the colorimeter cap disposed over the water sample container.

Referring now to FIG. 10, a perspective view of exemplary colorimeter 200 is shown with colorimeter cap 204 disposed over water sample container 220 and removably attached to base 202.

Referring now to FIG. 11, a flow chart of a first alternative embodiment of the method for determining the concentration of DTC in a water sample in accordance with the present invention is illustrated. As shown in FIG. 11, the first alternative embodiment of the method for determining the concentration of DTC in a water sample is designated generally by reference numeral 300. Preferred method 300 comprises some of the same initial steps and apparatus as the preferred water testing system described hereinabove and illustrated by FIGS. 1, 2, and 6. More particularly, preferred method 300 comprises providing a water testing system having a water sample container adapted to retain a water sample and a color indicator container adapted to dispense a color indictor. Preferred method 300 also comprises placing the water sample in a clean beaker or some other suitable water sample container. Preferably, if the water sample contains visible particles, the sample is filtered.

Still referring to FIG. 11, the water sample container (such as a clean vial or sample tube) is filled with 10 mL of the water sample and the water sample container and the water sample are placed into a colorimeter such as exemplary colorimeter 200 described hereinabove and illustrated in FIGS. 7-10. After placing the water sample container in colorimeter opening 206, it is covered with a light shield such as cap 204 and first button 210 is pushed to automatically determine an unreacted sample number or "blank value." After the unreacted sample number or "blank value" is determined, the water sample container is removed from colorimeter opening 206 and one (1) drop (approximately 0.04545 mL) of a color indicator such as copper sulfate solution is added to the 10 mL water sample from a color indicator drop bottle such as drop bottle 30 illustrated in FIG. 2. The preferred color indicator is adapted to change the color of the water sample when the water sample contains DTC. The water sample container is then preferably recapped and gently shaken or swirled for approximately thirty (30) seconds. Next, the water sample container is placed back into colorimeter opening 206 and covered with cap 204. Then, second button 212 is pushed and the colorimeter automatically determines the concentration of DTC in the water sample and displays the results on display 208. In the event that a water sample contains an extremely high concentration of DTC (for example, more than 1,000 PPM), then a smaller water sample may be tested after it is mixed with distilled or deionized water and the results of the tested sample are multiplied by the corresponding factor. By way of example, a 5 mL water sample may be mixed with 5 mL of distilled water, and the DTC concentration determined by the colorimeter multiplied by two (2) to obtain the actual DTC concentration in the water sample.

Although this description contains many specifics, these should not be construed as limiting the scope of the invention but as merely providing illustrations of some of the presently preferred embodiments thereof, as well as the best mode contemplated by the inventors of carrying out the invention. The invention, as described herein, is susceptible to various modifications and adaptations, and the same are intended to be comprehended within the meaning and range of equivalents of the appended claims.

What is claimed is:

1. A method for determining the concentration of sodium dimethyldithiocarbamate in a water sample, said method comprising:
    (a) providing a water testing system, said water testing system comprising:
        (1) a water sample container, said water sample container being adapted to retain the water sample;
        (2) a copper sulfate color indicator;
        (3) a color indicator container, said color indicator container configured to dispense the copper sulfate color indicator in solution form;
        (4) a colorimeter, said colorimeter configured to receive the water sample container and measure the water sample at a wavelength of approximately 450 nanometers or approximately 472 nanometers;
    (b) placing the water sample in the water sample container;
    (c) placing the water sample container in the colorimeter;
    (d) automatically determining a blank value;
    (e) adding the copper sulfate color indicator to the water sample;
    (f) placing the water sample container in the colorimeter; and
    (g) automatically determining the quantitative concentration of sodium dimethyldithiocarbamate in the water sample at a wavelength of approximately 450 nanometers or approximately 472 nanometers.

2. The method of claim 1 wherein the colorimeter comprises a light shield.

3. The method of claim 1 wherein the colorimeter comprises an opening adapted to receive the water sample container.

4. The method of claim 1 wherein the colorimeter comprises a display.

5. The method of claim 1 wherein the colorimeter is programmable.

6. The method of claim 1 wherein the colorimeter comprises a first button adapted to automatically provide a blank value for the water sample.

7. The method of claim 6 wherein the colorimeter further comprises a second button adapted to automatically provide a sodium dimethyldithiocarbamate concentration for the water sample.

8. The method of claim 1 wherein approximately 0.04545 mL of the copper sulfate color indicator in solution form is added to the water sample.

9. The method of claim 1 wherein the copper sulfate color indicator comprises copper sulfate pentahydrate.

10. A water testing system for determining the concentration of sodium dimethyldithiocarbamate in a water sample, said water testing system comprising:
    (a) a water sample container, said water sample container being adapted to receive the water sample;
    (b) a copper sulfate color indicator;
    (c) a color indicator container, said color indicator container configured to dispense the copper sulfate color indicator in solution form;
    (d) a colorimeter, said colorimeter configured to receive the water sample container and determine a blank value and a quantitative sodium dimethyldithiocarbamate concentration for the water sample at a wavelength of approximately 450 nanometers or approximately 472 nanometers;

wherein the colorimeter is configured to automatically determine the blank value and the quantitative sodium dimethyldithiocarbamate concentration for the water sample.

11. The water testing system of claim 10 wherein the colorimeter comprises a light shield.

12. The water testing system of claim 10 wherein the colorimeter comprises an opening adapted to receive the water sample container.

13. The water testing system of claim 10 wherein the colorimeter comprises a display.

14. The water testing system of claim 10 wherein the colorimeter is programmable.

15. The water testing system of claim 10 wherein the colorimeter comprises a first button adapted to automatically determine the blank value for the water sample.

16. The water testing system of claim 15 wherein the colorimeter further comprises a second button adapted to automatically determine the sodium dimethyldithiocarbamate concentration for the water sample.

17. The water testing system of claim 10 wherein the copper sulfate color indicator comprises copper sulfate pentahydrate.

* * * * *